United States Patent [19]

Walshe

[11] 4,254,302

[45] Mar. 3, 1981

[54] ELECTRONIC STETHOSCOPE

[76] Inventor: James C. Walshe, 9335 Lubec St., Downey, Calif. 90240

[21] Appl. No.: 45,828

[22] Filed: Jun. 5, 1979

Related U.S. Application Data

[63] Continuation-in-part of Ser. No. 914,732, Jun. 12, 1978, Pat. No. 4,170,717, which is a continuation of Ser. No. 770,224, Feb. 18, 1977, abandoned.

[51] Int. Cl.$^3$ ............................................. A61B 7/04
[52] U.S. Cl. .................................. 179/1 ST; 128/715
[58] Field of Search ..................... 179/1 ST; 455/351; 128/715

[56] References Cited

U.S. PATENT DOCUMENTS

| | | | |
|---|---|---|---|
| 2,145,449 | 1/1939 | Lockhart | 179/1 ST |
| 3,087,016 | 4/1963 | Dahl | 179/1 ST |
| 3,160,708 | 12/1964 | Andries et al. | |
| 3,182,129 | 5/1965 | Clark et al. | 179/1 ST |
| 3,247,324 | 4/1966 | Cefaly et al. | 179/1 ST |
| 3,539,724 | 11/1970 | Keesee | 179/1 ST |
| 3,939,421 | 2/1976 | Darringer et al. | 455/115 |

FOREIGN PATENT DOCUMENTS 1343675  10/1963  France ................................. 179/1 ST

OTHER PUBLICATIONS

A.M.C., "Model 320", Specification, 1979.

*Primary Examiner*—Charles E. Atkinson
*Assistant Examiner*—E. S. Kemeny
*Attorney, Agent, or Firm*—William W. Haefliger

[57] ABSTRACT

A portable, lightweight, self-contained stethoscope includes:
  (a) an enclosure containing a speaker, and having an acoustic wave outlet connectible to stethoscope flexible tubing,
  (b) an upright housing having upper and lower portions, and an intermediate portion therebetween, to provide a controllable and interdigitally graspable unit,
  (c) a transducer carried by the housing, the transducer including a microphone located to be placed in proximity to a patient's body,
  (d) circuitry in the housing and having an input terminal coupled with the transducer, said circuitry including amplifier means and filter means, and a battery power supply coupled with said circuitry, said circuitry having a first output terminal, that terminal and circuit controls protectively mounted between the upper and lower housing portions, and
  (e) flexible connection means coupling the first output terminal with said speaker,
  (f) the circuitry including an on-off switch and an indicator light on the housing to indicate when the battery power supply output is significantly dropping in value, and also to indicate when the on-off switch is in "ON" position.

6 Claims, 9 Drawing Figures

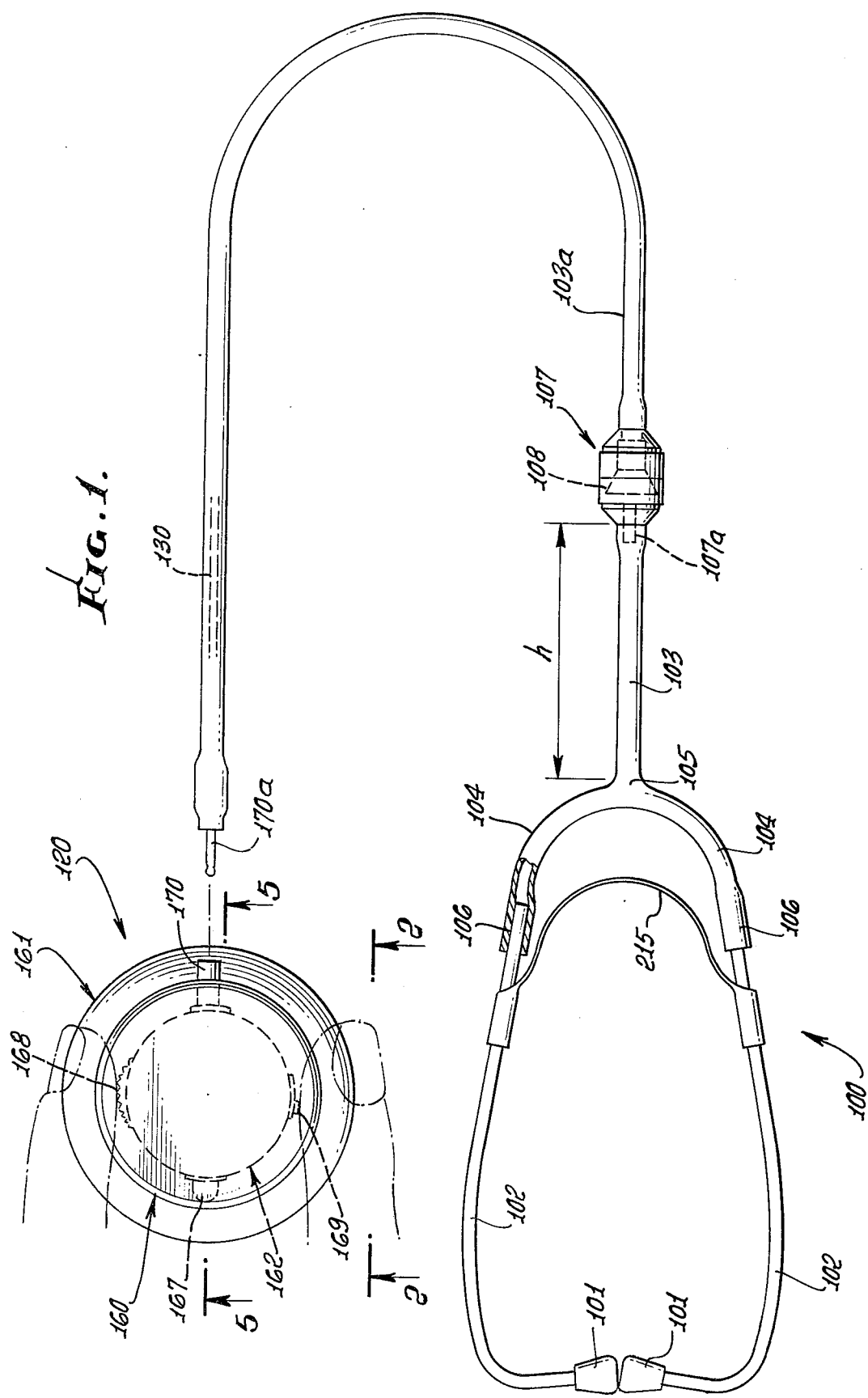

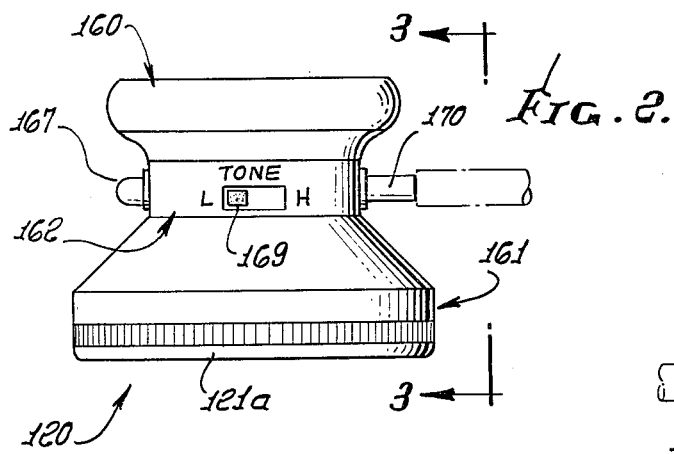
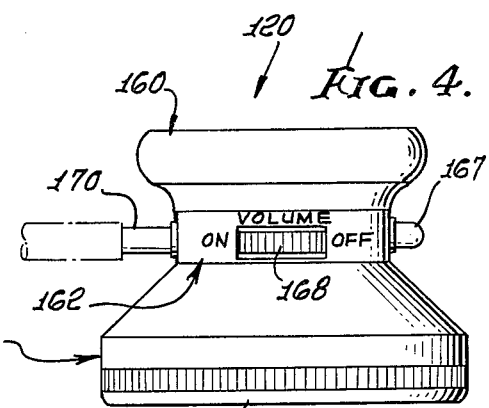
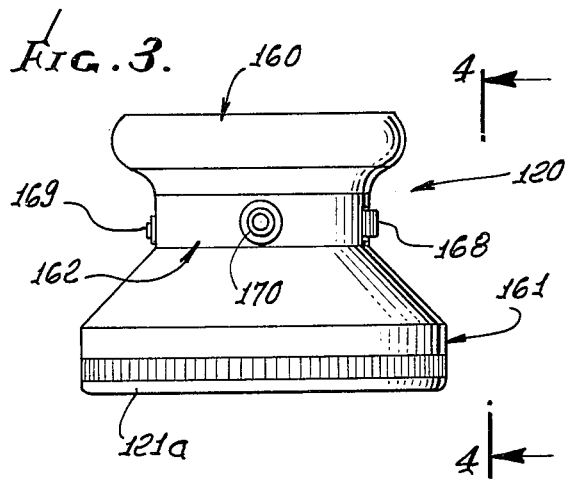
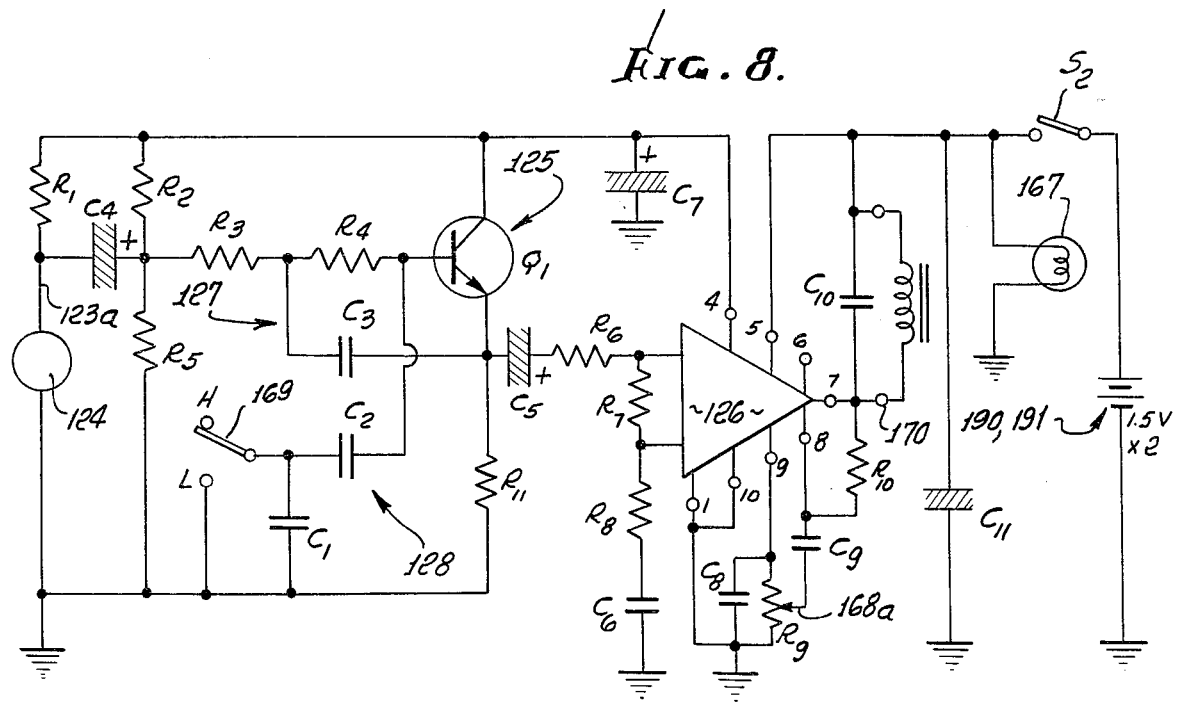

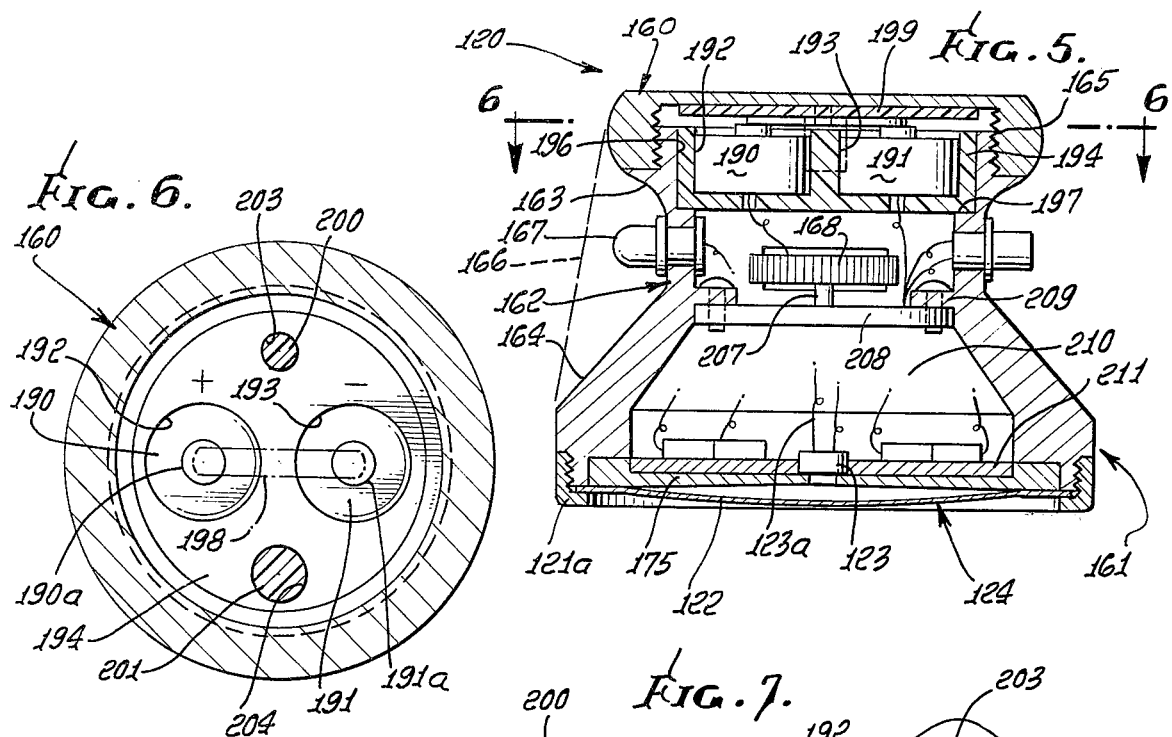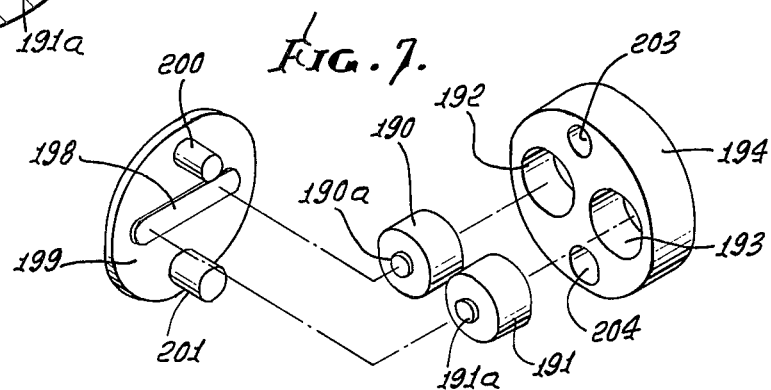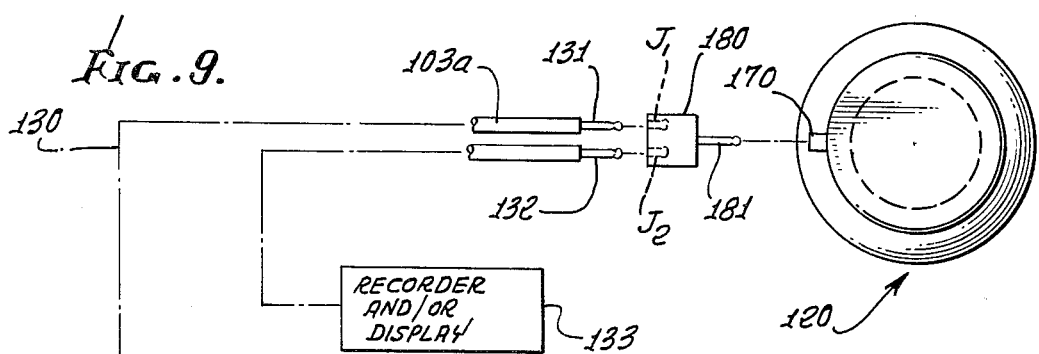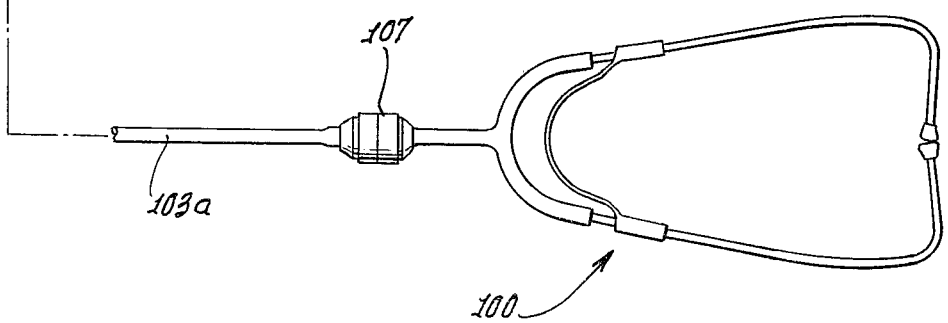

ELECTRONIC STETHOSCOPE

This application is a continuation-in-part of my prior application Ser. No. 914,732, filed June 12, 1978, now U.S. Pat. No. 4,170,717, which was a continuation of Ser. No. 770,224, filed Feb. 18, 1977, now abandoned.

BACKGROUND OF THE INVENTION

This invention relates generally to stethoscopes, and more particularly concerns an electronic stethoscope of wide adaptability and high efficiency.

Prior stethoscopes have suffered certain disadvantages, and have lacked advantages as are found in the present electronic unit. For example, no way was known, to my knowledge, to adapt electronic circuitry to an existing binaural pick-up in the unusually advantageous manner as now provided by the present invention. Also, the use of expensive circuitry is avoided, and an interdigitally graspable housing is provided to contain the circuitry and to be applicable to a patient, with means to indicate when battery power is dropping.

SUMMARY OF THE INVENTION

It is a major object of the invention to provide an electronic stethoscope affording numerous advantages, including adaptability to existing binaural pick-ups, high sensitivity including capability to selectively discriminate between body sounds of high and low frequency; light weight construction; selective recording capability; simplicity and other features and advantages as will appear. Fundamentally, the stethoscope comprises:

(a) an enclosure containing a speaker, and having an acoustic wave outlet port connectible to stethoscope flexible tubing, (b) an upright housing having upper and lower portions, and an intermediate portion therebetween to provide an interdigitally graspable unit, (c) a transducer carried by the housing, the transducer including a microphone located to be placed in proximity to a patient's body, (d) circuitry in the housing and having an input terminal coupled with the transducer, said circuitry including amplifier means and filter means, and a battery power supply coupled with said circuitry, said circuitry having a first output terminal, that terminal and circuit controls protectively mounted between the upper and lower portions, to provide a controllable and interdigitally graspable unit, (e) flexible connection means coupling the first output terminal with said speaker, and (f) the circuitry including an on-off switch and an indicator light on the housing to indicate when the battery power supply output is significantly dropping in value, and also to indicate when the on-off switch is in "ON" position.

As will appear, the body intermediate portion may carry sockets for interchangeable jack plugs leading to the speaker and to a recorder and/or associated display; the filter means may include two low pass filters, one or both of which may be selectively coupled to amplifier means to control the cut-off level of transmitted frequencies (for example, heart sounds may be isolated from other body sounds); and the speaker enclosure may be located between an extensible and flexible cord (connected to the circuit in the housing via a jack) and short-length stethoscope flexible tubing, as will appear.

Further, isolation of body sounds can be achieved through selective use of volume control and adjustable filtering. Such sounds include, but are not limited to, those produced by the heart, pulse, blood pressure and those associated with respiratory, peristalsis and fetal functions. Also, a battery to power the circuit may be carried in the housing, and a single control on the housing may control ON-OFF and gain (output volume) of the circuitry. Therefore no separate amplifier box or battery pack is required. Finally, the apparatus is light weight, may be hand-held and is portable.

These and other objects and advantages of the invention, as well as the details of an illustrative embodiment, will be more fully understood from the following description and drawings, in which:

DRAWING DESCRIPTION

FIG. 1 is a plan view showing stethoscope apparatus embodying the invention;

FIG. 2 is a side elevation taken on lines 2—2 of FIG. 1;

FIG. 3 is a right side view on lines 3—3 of FIG. 2;

FIG. 4 is a rear view on lines 4—4 of FIG. 3;

FIG. 5 is an enlarged section taken on lines 5—5 of FIG. 1;

FIG. 6 is a plan view taken in section on lines 6—6 of FIG. 5;

FIG. 7 is a perspective showing of a battery mount;

FIG. 8 is a diagram of circuitry embodied in the apparatus; and

FIG. 9 is a view of FIG. 1, showing a modification.

DETAILED DESCRIPTION

In the drawings, the stethoscope apparatus is shown to include a binaural acoustic stethoscope 100 having earpieces 101 connected to metallic ducts 102. A bowed spring 215 urges the ducts 102 toward one another. Acoustic waves are delivered to such ducts via a flexible duct 103 of length "h", and flexible tubular duct branches 104 connected at 105 to duct 103 and at 106 to ducts 102. Length "h" is preferably about 3 inches, and the length of duct 103a is about 15 inches, for best results, the total being substantially shorter than presently used ducts to provide quick finger access to a "chest piece" housing 120 to be discussed.

Coupled to the input end of duct 103 is a lightweight, end tapered enclosure 107 (which may consist of plastic material). The enclosure contains a small speaker 108, and has an outlet port communicating and in-line with the duct 103, whereby acoustic waves generated by the speaker are directly transmitted to the stethoscope duct 103. See FIG. 1 in this regard. The outlet port may for example be formed by a small tubular nipple 107a integral with enclosure 107 and telescopically fitting the end of flexible duct 103, whereby an existing, non-electronic stethoscope may be readily fitted to the enclosure 107, i.e. coupled to the electronic apparatus of the invention. An output amplifier may also be incorporated in the enclosure, if desired, and connected to the speaker. Enclosure 107, being streamlined, is effectively made part of the tubing 103, and tubing 103a, the latter being connected to the opposite end of housing 107 and having a diameter about the same as that of tubing 103, accommodating to the doctor's familiarly with stethoscope tubing.

Also shown in the drawings is an upright housing 120 having an annular upper portion 160, a relatively larger annular lower portion, 161, and a reduced diameter intermediate control portion 162 adapted to be interdigitally grasped, as between the doctor's first and second fingers. Referring to FIG. 5, the portions 161 and 162 may be integral to define a hollow body, with tapers at 163 and 164 above and below portion 162; and upper portion 160 may define a cap thread-connected at 165 to the body. In addition to being interdigitally graspable, mid-portion 162 provides a means to carry controls adjacent the doctor's fingers for accessibility, the controls being protectively confined between enlarged upper and lower portions 160 and 161, so that if the housing 120 is dropped, the controls will not strike the floor. Note protective line 166, at the inner side of which the light 167 is confined, for example, in FIG. 5. Light 167 may comprise an LED, or a cup-shaped housing or lens for the LED or other lamp, mounted to mid-portion 162 as shown. Other controls include a combined ON-OFF switch and volume control 168 shown in FIG. 4; and a hi-lo frequency control 169 shown in FIG. 2. A jack connection (female) is also shown at 170 mounted on the housing mid-portion, generally diametrically opposite the light 167. Controls 168 and 169 are also generally diametrically opposite one another, at 12 and 6 o'clock positions relative to the 3 and 9 o'clock positions of the light and jack whereby the doctor's fingers may extend adjacent controls 168 and 169 without interfering with the jack 170, and leaving the light 167 exposed for viewing at all times. FIG. 1 shows this, as well as jack plug 170a.

The housing lower portion 161 defines a body piece which includes an annular ring 121a made of material to be comfortably (for example with no chill) placed against a patient's body or clothing covering same. A thin diaphragm 122 extends across the opening formed by ring 121a and may be part of, or acoustically coupled to, a pick-up microphone 123. The microphone and/or diaphragm may be considered as a transducer 124 operable to convert acoustic pulses, i.e. heart beats, to electrical signals at microphone output 123a. The housing 120 is readily hand-manipulated to place the wide-mouthed body piece against the patient's body, or clothing covering same, so that the microphone is able to efficiently pick-up body sounds. A disc 175 mounts the microphone and provides a back-up for the diaphragm 122.

Extending the description to FIG. 8, the housing contains circuitry having an input terminal (i.e. at 123a) coupled to the transducer 124, the circuitry including amplifier means and filter means and at least one output terminal. As seen in FIG. 8, the amplifier means includes an input section 125 and an output section 126, and the filter means includes low pass filter sections 127 and 128.

While only one output terminal as at 170 may be used, FIG. 9 shows first and second output terminals at $J_1$ and $J_2$ may advantageously be defined by jack connection sockets in adapter 180 having a jack plug 181 insertible in socket 170. Either of the sockets $J_1$ and $J_2$ may be coupled to the speaker 108, as via flexible connection means such as flexible duct or cord 103a. The latter has a jack plug 131 at one end, the plug interfitting either socket $J_1$ and $J_2$. An electrical wire 130 within the cord connects the plug to the speaker 108, (or amplifier) within enclosure 107. A second jack plug 132 is sized to fit either socket $J_1$ and $J_2$, and is connected with a recording device, and/or an associated display, indicated at 133. Jack plug 131 may be directly connected to socket 170.

The manually controllable element, such as slide button 169 on the housing, is connected with the low-pass filter means to adjust same between a first position in which both filters 127 and 128 are connected to amplifier section 125, and a second position in which only filter section 127 is connected to amplifier section 125. Accordingly, the filter means is adjustable to cut-off at one frequency level when both filters are interconnected, and another level when only one filter is operative, whereby the user may more easily discriminate between different body sounds.

The circuitry also includes adjustable means to control the amplitude of the signal transmitted to the speaker 108, and manually controllable part 168 is located on the housing to adjust the adjustable means. The latter may include a potentiometer resistor indicated at $R_9$ in FIG. 8 as coupled between amplifier 126 and ground. Rotor 168 on the housing controls the potentiometer wiper 168a engageable with resistor $R_9$.

An on-off switch is indicated at $S_2$, and may also be controlled by rotor 168, i.e. to turn ON when the rotor is initially rotated from OFF position (thereafter, turning of the rotor controls the potentiometer).

Typical circuit elements are indicated as follows:
Q-1—25C373
126—μpc 12G
R-1—1K
R-2—82K
R-3—39K
R-4—39K
R-5—68K
R-6—1K
R-7—1K
R-8—200Ω
R-9—50K
R-10—30K
R-11—1K
C-1—0.0068 μF
C-2—0.047 μF
C-3—0.1 μF
C-4—10 μF
C-5—1 μF
C-6—10 μF
C-7—10 μF
C-8—0.01 μF
C-9—10 μF
C-10—1 μF
C-11—10 μF
Frequency Response:
(L)—20–200 Hz
(H)—50–1,500 Hz
Battery: two 1.5 V. silver oxide cells.

Referring to FIGS. 5–7, the two replaceable batteries 190 and 191 are typically removably received in wells 192 and 193 in a circular holder 194. The holder is in turn removably received in the body bore 196, and against shoulder 197. A metallic terminal strip 198 on a disc 199 engages the battery terminals 190a and 191a, when cap 160 is in place, to connect the two batteries in series. Different sized locater studs 200 and 201 on the disc 199 interfit locater stud holes 203 and 204 in the holder 194.

Rotor 168 is rotatably mounted at 207 on a partition 208 attached to body flanges 209, within the body hollow 210. That partition may carry circuit elements. Other circuit elements are mounted on a circuit board 211 that carries the microphone 123, that board extending adjacent disc 175, as seen in FIG. 5.

The filters 127 and 128, for best results, pass between about 20 and 300 Hz in "Lo" position of switch 169, and between 40 and 700 Hz in "HI" position of that switch.

Referring again to FIG. 9, the use of the dual jack sockets J₁ and J₂ enables use by two doctors for dual diagnosis purposes, and also for teaching (both doctors listening, simultaneously).

I claim:

1. In a portable, lightweight, self-contained electronic stethoscope, the combination comprising
   (a) a lightweight enclosure containing a speaker,
   (b) a housing separate and remote from said enclosure, the housing having upper and lower portions, and an intermediate portion between said upper and lower portions,
   (c) a transducer carried by the housing, the transducer including a microphone located to be placed in proximity to a patient's body, the microphone having an exposed diaphragm to acoustically couple to the patient's body, the diaphragm located on said lower portion of the housing,
   (d) circuitry in the housing and having an input terminal coupled with the transducer, said circuitry including amplifier means and filter means, and a battery power supply in the housing upper portion and coupled with said circuitry, said circuitry having a first output terminal,
   (e) flexible electrical connection means outside the housing and coupling said first output terminal with said speaker, said connection means including a flexible cord,
   (f) said circuitry including adjustable means to control the amplitude of the signal transmitted to the speaker, there being a manually controllable part on the housing connected with said adjustable means which includes a potentiometer coupled to said amplifier means, said part projecting from one side of the housing,
   (g) said filter means comprising an adjustable low-pass filter means, there being a manually controllable element on the housing and connected with said adjustable low-pass filter means to adjust same, said element being movable between two positions,
   (h) said enclosure having a tubular nipple defining only a single acoustic wave outlet port connected to a single flexible tubing of the stethoscope, said single tubing branching to become two tubings at a location spaced from the enclosure, the speaker acoustically facing toward said single outlet port,
   (i) said single outlet port being in lengthwise alignment with said single flexible tubing, and said flexible electrical connection means approaching said enclosure in alignment with said outlet port and said single flexible tubing, whereby the enclosure effectively becomes an extension of said single tubing and of said flexible electrical connection means,
   (j) the housing intermediate portion having a reduced cross section as compared with said upper and lower portions to provide an interdigitally graspable unit, with said part and said manually controllable element located proximate one another yet projecting in different directions so as to be manipulable by the fingers of the user's hand,
   (k) said circuitry including an on-off switch controlled by said part, and including an indicator light on the housing to indicate when the battery power supply output is significantly dropping in value, and also to indicate when the on-off switch is in "ON" position,
   (l) the first output terminal being defined by a jack receptable on said intermediate portion of the housing, and said light, said filter manually controllable element and said part are also located on said reduced cross section intermediate portion of the housing which is annular so that said jack receptacle, said light, said manually controllable element and said part all project in different directions.

2. The combination of claim 1 wherein said battery power supply includes first and second batteries, and there being a retainer bracket electrically interconnecting said batteries, the upper portion of the housing including a removable cap biasing said bracket to engage terminals defined by the batteries when the cap is connected to the remainder of the housing.

3. The combination of claim 1 wherein said enclosure has opposite ends that define frusto-conical surfaces which are conical.

4. The combination of claim 1 including additional flexible tubing containing said flexible connection, said additional tubing having about the same diameter as said flexible tubing.

5. A portable, lightweight, self-contained stethoscope includes:
   (a) an enclosure containing a speaker, and having an acoustic wave outlet connectible to stethoscope flexible tubing,
   (b) a housing having upper and lower portions, and an intermediate portion therebetween, to provide a controllable and interdigitally graspable unit,
   (c) a transducer carried by the housing, the transducer including a microphone located to be placed in proximity to a patient's body,
   (d) circuitry in the housing and having an input terminal coupled with the tranducer, said circuitry including amplifier means and filter means and manual controls therefor, and a battery power supply coupled with said circuitry, said circuitry having a first output terminal, that terminal and circuit controls protectively mounted between the upper and lower housing portions and on and projecting outwardly from said intermediate portion of the housing which is of reduced cross section relative to the cross sections of said upper and lower portions, and
   (e) flexible connection means coupling the first output terminal with said speaker,
   (f) the circuitry including an on-off switch and an indicator light on the housing to indicate when the battery power supply output is significantly dropping in value, and also to indicate when the on-off switch is in "ON" position, said switch and said light projecting in different directions,
   (g) said power supply including two batteries removably contained in a holder in the housing, and a connector strip interconnecting said batteries, the upper portion of the housing including a cap which is removable to expose said batteries for replacement.

6. The combination of claim 1 including an adapter having a first jack plug received in said jack receptacle, the adapter having two additional jack receptacles connected with said first jack plug, said two additional jack receptacles respectively adapted to receive a second jack plug associated with said flexible electrical connection and a third jack plug connected with recording and/or an associated display apparatus.

* * * * *